(12) United States Patent
Kreber et al.

(10) Patent No.: US 10,926,015 B2
(45) Date of Patent: *Feb. 23, 2021

(54) CASSETTE MODULE

(71) Applicant: Fresenius Medical Care Deutschland GmbH, Bad Homburg (DE)

(72) Inventors: Stefan Kreber, Saarbruecken (DE); Manfred Weis, St. Wendel (DE); Marina Wenke, St. Wendel (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 122 days.

This patent is subject to a terminal disclaimer.

(21) Appl. No.: 14/910,761

(22) PCT Filed: Aug. 6, 2014

(86) PCT No.: PCT/EP2014/002167
§ 371 (c)(1),
(2) Date: Feb. 8, 2016

(87) PCT Pub. No.: WO2015/018524
PCT Pub. Date: Feb. 12, 2015

(65) Prior Publication Data
US 2016/0184502 A1  Jun. 30, 2016

(30) Foreign Application Priority Data
Aug. 9, 2013  (DE) ..................... 10 2013 013 414.5

(51) Int. Cl.
*A61M 1/16* (2006.01)
*A61M 1/14* (2006.01)
(Continued)

(52) U.S. Cl.
CPC ............ *A61M 1/1601* (2014.02); *A61M 1/14* (2013.01); *A61M 1/267* (2014.02); *A61M 1/34* (2013.01);
(Continued)

(58) Field of Classification Search
CPC ...... A61M 1/1601; A61M 1/14; A61M 1/267; A61M 1/34; A61M 1/3403; A61M 1/165;
(Continued)

(56) References Cited

U.S. PATENT DOCUMENTS

| 5,350,357 A | 9/1994 | Kamen et al. |
| 2007/0278155 A1* | 12/2007 | Lo ........................... A61M 1/16 210/646 |

(Continued)

FOREIGN PATENT DOCUMENTS

| EP | 0129554 | 12/1988 |
| WO | WO 2008/106440 | 9/2008 |

*Primary Examiner* — Bobby Ramdhanie
*Assistant Examiner* — Donovan Bui-Huynh
(74) *Attorney, Agent, or Firm* — Jacobson Holman, PLLC

(57) ABSTRACT

The present invention relates to a cassette module for controlling fluid flows, in particular for use in blood treatment systems or in infusion systems, wherein the cassette module has at least one first functional layer and at least one second functional layer, wherein the first functional layer has means for the flow guidance of at least one fluid flow, and wherein the cassette module furthermore has at least two membranes of which the first is in contact with the means for the flow guidance of a fluid flow, and wherein the second functional layer is arranged between the two membranes and has means for generating an underpressure between the membranes.

11 Claims, 1 Drawing Sheet

(51) Int. Cl.
*A61M 1/26* (2006.01)
*A61M 5/165* (2006.01)
*B29C 65/16* (2006.01)
*A61M 1/34* (2006.01)
*B23K 26/244* (2014.01)
*B29C 65/00* (2006.01)

(52) U.S. Cl.
CPC .......... *A61M 1/3403* (2014.02); *A61M 5/165* (2013.01); *B23K 26/244* (2015.10); *A61M 2005/1657* (2013.01); *A61M 2205/12* (2013.01); *A61M 2205/126* (2013.01); *A61M 2205/15* (2013.01); *A61M 2205/3331* (2013.01); *A61M 2207/00* (2013.01); *B29C 65/1635* (2013.01); *B29C 65/1683* (2013.01); *B29C 66/53421* (2013.01); *B29C 66/727* (2013.01)

(58) Field of Classification Search
CPC ........ A61M 2205/12; A61M 2205/126; A61M 2205/15; A61M 2205/3331; A61M 1/30; A61M 1/1623; A61M 1/1652; A61M 1/1672; A61M 1/304; A61M 5/165; A61M 2005/1657; A61M 2205/1657; A61M 16/0616; A61M 16/207; B23K 26/244; B23K 26/18; B29C 65/1635; B29C 65/1683; B29C 66/53421; B29C 66/727; B29C 65/16; B29C 66/1122; B29C 66/5346; B29C 66/543; B29L 2031/753
See application file for complete search history.

(56) References Cited

U.S. PATENT DOCUMENTS

| | | | | |
|---|---|---|---|---|
| 2009/0137940 | A1* | 5/2009 | Orr | A61M 1/106 604/6.11 |
| 2011/0028902 | A1* | 2/2011 | Siefert | A61M 5/14224 604/152 |
| 2011/0228902 | A1 | 9/2011 | Virta | |
| 2012/0167673 | A1* | 7/2012 | Farjam | B01L 3/502715 73/64.56 |
| 2012/0177506 | A1* | 7/2012 | Orter | A61M 1/1053 417/53 |
| 2013/0118970 | A1* | 5/2013 | Beden | A61M 1/1037 210/321.6 |

* cited by examiner

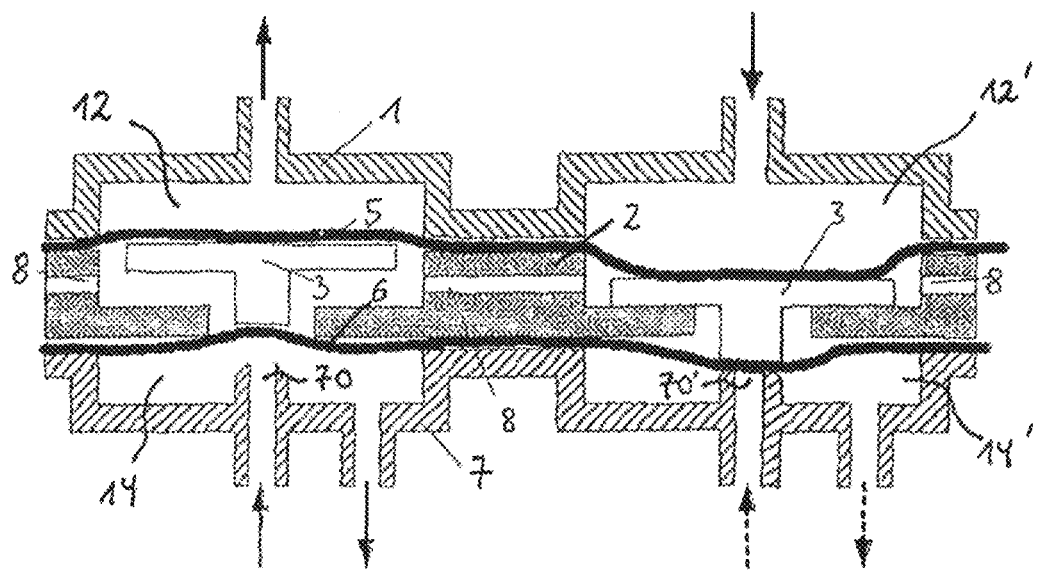

CASSETTE MODULE

The present invention relates to a cassette module for controlling fluid flows, in particular for use in blood treatment systems or in infusion systems.

Cassette modules are known from the prior art, for example for use in dialyzers, in particular in hemodialysis or peritoneal dialysis. These cassette modules have the task of being able to control or convey liquid flows, in particular blood, dialyzate or other liquids relevant to treatment, with the aid of integrated functional units within the framework of the treatment. Such functional units are, for example, valves, pumps, channels, etc. The flows of blood, dialyzate and other liquids relevant to treatment can be controlled by them.

Cassette modules can be manufactured in mass production due to the comparatively inexpensive plastics used and are frequently used as disposable articles.

The named valve functions and pump functions are known in cassette modules from the prior art. Flow channels and/or openings can be formed in cassette bodies which can be brought into contact with a movable membrane in order to be able to provide the named function in this manner. It is thus conceivable, for example, to use the membrane for pumping a liquid as well as to cover an opening etc. by the membrane in dependence on its position and thus to provide a valve function.

The deflection of the membrane itself can take place by a pneumatic actuation, for example.

A cassette module is known from EP 0 129 554 B1 which comprises two plates between which a movable membrane is arranged. This is controlled by a pneumatic actuation. For this purpose, one of the plates of the cassette module is designed as an actuator plate which is designed with channels and chambers in which excess pressure or vacuum can be generated as required.

U.S. Pat. No. 5,350,357 discloses a cassette module which can be operated via a pneumatic actuator module at the machine side. The cassette module comprises a base body which is covered by a membrane at its front side and rear side. The pneumatic control and thus the control of the liquid flows within the cassette module takes place via the pneumatic deflection of one of the membranes.

WO 2008/106440 A1 finally discloses a cassette which comprises three plates, wherein the liquid paths within the cassette module are substantially arranged on the center plate which is arranged between the two outwardly disposed plates. The required pump functions and valve functions can be generated via individual membranes. The deflection of the membranes takes place via pneumatic connections which are arranged in one of the plates.

In the cassette modules known from the prior art, the liquid to be conveyed is separated from the drive side, i.e. from the pneumatic side, by the named membrane.

If a tear of these membranes occurs, this does not result in a contamination of the conveyed liquid such as blood or dialyzate with the pneumatic medium or in a loss of blood or dialyzate which flows through the tear onto the pneumatic side of the cassette module.

It is thus the object of the underlying invention to further develop a cassette module of the initially named kind such that the probability of a contamination of the fluid located in the cassette module is reduced.

This object is satisfied by a cassette module having the features of claim 1. Provision is accordingly made that the cassette module has at least one functional layer and at least one second functional layer, wherein the first functional layer has means for the flow guidance of at least one fluid flow such as blood or dialyzate, and wherein the cassette module furthermore has at least two membranes of which the first cooperates with the means for the flow guidance of a liquid flow, and wherein the second functional layer is arranged between the two membranes and has means for generating an underpressure between the membranes.

In accordance with the invention, at least two membranes are thus provided which separate the fluid flow (liquid or gas) which can be controlled or conveyed by means of the cassette module from an actuator medium such as compressed air or a liquid.

A coupling of the two membranes is achieved by the underpressure present between the membranes and an unwanted positioning such as the sagging of one of the membranes is prevented. If a membrane is moved by the actuator medium, such as compressed air, the other membrane is taken along accordingly.

It is ensured by the coupling of the two membranes, caused by the vacuum, that the one membrane follows the other membrane directly, i.e. both membranes are coupled in their movement procedures. A partial closure of a fluid channel by a sagging film in the case of underpressure can thus be effectively avoided.

The first functional layer contains means such as valve means or pump means to control or regulate flow procedures, in particular of liquids relevant to the treatment, in cooperation with the first membrane.

The cassette module can have a third functional layer which has means for actuating the second membrane and which cooperates in this form with the second membrane. The third functional layer can, for example, have chambers and/or flow passages which can be acted on by excess pressure or underpressure so that, depending on whether an excess pressure or underpressure is present, a movement of the second membrane takes place, and also of the second membrane due to the named coupling. In this manner, for example, a conveying of a fluid by a pump movement is conceivable or also the closing or opening of valves, etc.

The terms "excess pressure" and "underpressure" are not necessarily to be understood as absolute values relative to atmospheric pressure, but also as relative values.

An excess pressure or underpressure in a chamber thus only means a relative pressure relative to the other chamber, for example. It is thus conceivable, for example, that a liquid flows into a chamber by the operation, whereby an excess pressure arises in this chamber relative to the other chamber without vacuum necessarily being present in the other chamber.

The use of vacuum, i.e. an underpressure relative to atmospheric pressure, is nevertheless naturally also conceivable and also covered by the invention.

The means for the flow guidance of a fluid flow can be any desired means by which influence can be taken on the flow of the fluid. This includes, for example, one or more channels, valves or pumps or valve sections or pump sections.

The means for generating an underpressure between the membranes can include one or more channels which are or can be connected to a vacuum pump or the like. It is thus conceivable, for example, that a vacuum pump is provided at the machine side which is connected to the cassette module such that a vacuum can be generated between the two membranes.

Provision is preferably made that the first membrane directly contacts the first functional layer and the second functional layer and/or that the second membrane directly contacts the second and third functional layers.

To achieve an improved force transmission from one membrane to the other membrane, it is conceivable that at least one means for improving this force transmission such as a plunger or a plunger disk is present between the two membranes.

Provision can furthermore be made that the plunger or the disk provided with the plunger is configured such that the plunger or the disk cooperates with the means for the flow guidance via the first membrane in at least one position. It is thus conceivable, for example, that a valve can be reliably opened or closed due to the presence of the plunger or of a plunger plate. The sealing function can be taken over by the first membrane; the transmission of the closing force takes place at least partly via the plunger disk.

Provision can furthermore be made that the cassette module, in particular the second functional layer, has at least two marginal regions, in particular at oppositely disposed edges, into which the means for generating an underpressure between the membranes open. The means for generating an underpressure can be formed, for example, by channels which extend in the second functional layer and which can be connected to a vacuum pump or the like so that an underpressure can be achieved between the membranes.

The functional layers can comprise a flexurally stiff material and the membranes can comprise an elastomer material.

The membranes are flexible so that they can be moved by the actuator medium, on the one hand, and can carry out the required deflections at the fluid side, on the other hand.

The present invention furthermore relates to a machine, in particular to a blood treatment machine or to an infusion machine, having at least one slot in which at least one cassette module in accordance with one of the claims 1 to 13 is located.

The machine can, for example, be a dialysis machine or also an apparatus for carrying out an infusion. It is conceivable that the dialysis machine is hemodialysis machine or a peritoneal dialysis machine.

The machine can have underpressure means such as a vacuum pump or the like, for example, which is in communication with the means for generating an underpressure between the membranes and generates an underpressure there in the operation of the machine so that the membranes lie as close to one another as possible and, where possible, contact a force transmission means in the event one is located between the membranes.

A conceivable method of manufacturing the cassette module comprises the use of laser radiation. It is conceivable in this respect that the connection of the membrane to at least one further component of the cassette module takes place by means of transmission welding using a laser, wherein provision is preferably made that the heating of the at least one layer of the membrane absorbing the laser light takes place.

It is conceivable that the membrane has at least one layer transmitting the laser light and at least one layer absorbing the laser light, wherein the layer absorbing the laser light forms the connection region of the membrane for at least one further component of the cassette module. A monolayer design with an absorber for the laser light is also covered by the invention.

Further details and advantages of the invention will be explained in more detail with reference to an embodiment shown in the drawing.

The only FIGURES shows a longitudinal sectional view through a cassette module in accordance with the invention.

The first functional layer is marked by the reference numeral 7 and the second functional layer is marked by the reference numeral 2.

Reference numeral 1 marks the third functional layer.

As can be seen from the FIGURE, the second functional layer 2 is located between the first functional layer 7 and the third functional layer 1.

Furthermore, a first membrane 6 is located between the second functional layer 2 and the first functional layer 7 and a second membrane 5 is located between the third functional layer 1 and the second functional layer 2.

Reference numeral 8 marks vacuum channels which extend through the second functional layer 2 and which have the purpose of providing or maintaining a vacuum between the two membranes 5, 6.

As can furthermore be seen from the FIGURE, a respective one plunger or a respective one plunger plate 3 is located between the membranes 5, 6 in both chambers shown which equally serves as a valve for closing or releasing an opening 70, 70 in the first functional layer 7.

In the state of the cassette module inserted into a machine, a vacuum is applied to the channel 8 by a vacuum pump or the like of the machine so that the two membranes 5, 6 tightly contact one another or tightly contact the plunger or the plunger plate 3.

As can further be seen from the FIGURE, means for the flow guidance of at least one liquid flow such as blood, dialyzate, an infusion solution, etc. are located in the first functional layer 7, wherein in the embodiment shown here, the means are configured in the form of a valve which allows or prevents a throughflow of the chambers 14, 14' of the cassette module.

As can further be seen from the FIGURE, the valve block or the cassette module designed as a valve block has two such valves, wherein the valve having the opening 70 in the chamber 14 of the cassette module shown at the left being open and the valve having the opening 70' in the chamber 14' of the cassette module shown at the right being closed.

The opening of the valve takes place in that underpressure is generated in the pneumatic chamber 12 as shown by an arrow. This has the result that the second membrane 5 and, due to the vacuum present between the membranes, also the first membrane 6 as well as also the plunger plate 3 are moved upwardly, whereby the opening 70 is released by the membrane 6. A fluid flow through the fluid chamber 14 is thereby made possible. As already stated above, the terms excess pressure and overpressure do not necessarily mean absolute values relative to atmospheric pressure, but can also be understood as values relative to one another.

It is thus conceivable, for example, that an underpressure in the chamber 12 does not only mean that vacuum is applied by a pump in the chamber. It can also mean that a liquid is flowed into the chamber 14 by the operation of the cassette without, however, actuation taking place against this in the chamber 12.

The membranes 5, 6 are also deflected in this case and the chamber 12 represents the underpressure side with respect to the chamber 14 without vacuum necessarily having to be present in the chamber 12.

The pressure in the functional layer 2 is lower than in the layers 1 and 14.

In the chamber 12' of the cassette module shown at the left, in contrast, an excess pressure is generated, as is symbolized by the arrow shown which symbolizes the inflow of a pneumatic fluid, in particular of compressed air. The two membranes 5, 6 as well as also the plunger plate 3 shown at the right are thereby urged downwardly and the opening 70' is closed by means of the first membrane 6. The chamber 14' can thus not be flowed through by a fluid, as is indicated by the dashed arrows.

The cassette module shown in the FIGURE is a valve block. Any desired other functionalities are generally also covered by the invention such as a pump function or the like.

The functional layers 1, 2, 7 comprise a flexurally stiff plastic, i.e. a stable-shape plastic, whereas the membranes 5, 6 are designed as flexible, preferably elastic membranes so that the desired flow guidance can be set.

It can further be seen from the FIGURE that both the first functional layer 7 and the third functional layer 1 have flared portions which form chambers 12, 14, 12', 14' which serve, on the one hand, for controlling the membranes via an actuator medium such as compressed air and, on the other hand, for controlling a fluid flow such as blood, dialyzate, infusate, etc.

The cassette module shown is naturally not only suitable for controlling a liquid flow, but also, for example, to control a gas flow.

The control via the chambers 12, 12 also does not necessarily have to take place using a gas or compressed air, but can rather likewise take place via a fluid, i.e. hydraulically.

The valve shown or the plunger plate 3 is brought into the one or other end position by the excess pressure or underpressure in the chambers 12, 12' and closes or opens a fluid circuit or the opening 70, 70' with its side opposite the pneumatic system or hydraulic system in dependence on its instantaneous position.

The end positions can, for example, be formed by surfaces or functional layers such as by the second functional layer. In the right chamber, the plate-shaped region of the plunger plate abuts the second functional layer so that an end position is thereby defined.

The control circuit, for example the pneumatic circuit, and the fluid circuit, for example a circuit for conveying blood, dialyzate, etc., are reliably separated by the presence of two membranes 5, 6 so that no contamination can occur on the tearing of a membrane.

Due to the fact that there is a vacuum present between the membranes 5, 6 and the one membrane thus follows the movement of the other membrane, a reliable opening of the valve or of the opening 70, 70' can also be achieved when underpressure is present on the fluid side, i.e. on the side of the chamber 14, 14' or of the opening 70, 70'. Otherwise, the case could occur that, with a closed valve and an applied underpressure, the passage 70, 70' could no longer be opened by applying underpressure in the chamber 12, 12'.

The two membranes 5, 6 are preferably only connected to one another by the application of an underpressure.

The membrane 5 is preferably in direct contact with the functional layers 1 and 2 and the membrane is preferably in direct contact with the functional layers 2 and 7.

It is generally also possible to provide additional coupling means, such as a weld, via which the membranes can be connected to one another. A preferred embodiment of the invention, however, comprises fully dispensing with the named weld.

At least one sensor is preferably provided in the channel 8 or in a line element connected thereto and said sensor can measure the pressure and/or the flow in the channel. It is thus possible to be able to recognize a rupture of either the membrane 5 or the membrane 6 or of both membranes at an early stage, preferably by the machine, and particularly preferably directly after the upgrading and still before the start of treatment. A rupture can, however, also be recognized via a variable power pick-up of the vacuum pump means which is connected to the functional layer.

If it is, for example, found that the desired vacuum cannot be maintained in the channel 8 and thus also not in the regions located between the membranes 5, 6, this can be due to the fact that a rupture is present in one or both of the membranes 5, 6. In this case, the cassette module preferably designed as a disposable is to be replaced with a functional module.

It is pointed out at this point that the term "membrane" is to be understood widely and covers any areal and movable material which can carry out the named functions. The membranes can, for example, be configured as films.

They are preferably not permeable for the fluid or also for the actuator medium. There are furthermore preferably largely impermeable for gas so that the vacuum can be easily maintained.

Further advantages of the invention comprise an increased security of the valve function shown also being present on possible welding defects on the connecting of the membranes 5, 6, no partial closure of the fluid channel by a sagging film being able to be present in the case of underpressure and a complete omission of the welding process of the films to the valves being possible.

The movement or valve function exerted by the second membrane 5 takes place faster and more precisely due to the plunger disk 3 located between the membranes 5, 7. This allows higher clock rates of the valve switching, which is desirable.

The invention claimed is:

1. A cassette module for guidance of fluid flows, the cassette module comprising
   a first functional layer, a second functional layer, and a third functional layer, wherein each of the first, second, and third, functional layers comprises a flexurally stiff material, and wherein the first functional layer has means for guidance of a fluid flow,
   a first membrane having at least one layer and a second membrane having at least one layer, wherein the second functional layer is arranged between the first and second membranes, wherein each of the first and second membranes is an elastic membrane, and wherein the first membrane cooperates with the means for guidance of a fluid flow, wherein the second functional layer is arranged between the first and second membranes and has means for generating an underpressure between the first and second membranes, and wherein the third functional layer has means for actuating the second membrane and with which the second membrane cooperates, and
   a movable plunger or plunger disk present between the first and second membranes for transmitting force from the first membrane to the second membrane.

2. A cassette module in accordance with claim 1, characterized in that the means for actuating the second membrane are pneumatic means or hydraulic means in which excess pressure or underpressure is present or can be generated.

3. A cassette module in accordance with claim 1, characterized in that the means for guidance of fluid flow has one or more channels, valve sections and pump sections.

4. A cassette module in accordance with claim 1, characterized in that the means for generating an underpressure between the first and second membranes comprises one or more channels which are or can be connected to a vacuum pump.

5. A cassette module in accordance with claim 1, characterized in that the first membrane directly or indirectly contacts the first functional layer, and the first and second membranes directly or indirectly contact the second functional layer.

6. A cassette module in accordance with claim 1, characterized in that the at least one second membrane directly or indirectly contacts the second and the third functional layers.

7. A cassette module in accordance with claim 1 characterized in that the plunger or plunger disk is configured such that it cooperates with the means for guidance of a fluid flow in at least one position.

8. A cassette module in accordance with claim 1, characterized in that at least one of (a) the cassette module has at least two edges arranged opposite or adjacent to one another, into which the means for generating an underpressure between the first and second membranes opens, and (b) the cassette module has at least one sensor intended for measurement of pressure present between the first and second membranes.

9. A machine, comprising at least one slot in which at least one cassette module in accordance with claim 1 is located, respectively, such that blood flow through the means for guidance of a fluid flow is controlled by deflection of the first and second membranes.

10. A machine in accordance with claim 9 further comprising at least one of
   underpressure generating means in communication with the means for generating an underpressure between the first and second membranes and
   at least one sensor present in at least one of the machine and the cassette module for measuring pressure between the first and second membranes or a parameter correlated therewith.

11. A cassette module in accordance with claim 1, characterized in that the means for actuating the second membrane are chambers or channels in which excess pressure or underpressure is present or can be generated.

* * * * *